United States Patent [19]

Marshall et al.

[11] Patent Number: 4,516,968
[45] Date of Patent: May 14, 1985

[54] CATHETER SHIELD AND METHOD OF USE

[76] Inventors: Charles A. Marshall, 2937 - 181st Ave., N.E, Seattle, Wash. 98052; Jeremiah B. Ray, 4546 Thacksray Pl., NE., Seattle, Wash. 98105

[21] Appl. No.: 425,494

[22] Filed: Sep. 28, 1982

[51] Int. Cl.$^3$ .............................................. A61M 25/02
[52] U.S. Cl. ............................ 604/174; 128/DIG. 26
[58] Field of Search ........................ 604/174, 176–180; 128/DIG. 26

[56] References Cited

U.S. PATENT DOCUMENTS

| | | |
|---|---|---|
| 703,290 | 6/1902 | Mulford . |
| 3,234,941 | 2/1966 | Tucker . |
| 3,487,837 | 2/1967 | Petersen ...................... 128/DIG. 26 |
| 3,605,752 | 9/1971 | Schlesinger . |
| 3,682,180 | 8/1972 | McFarlane . |
| 3,683,911 | 8/1972 | McCormick . |
| 3,900,026 | 8/1975 | Wagner ............................ 604/174 X |
| 3,957,048 | 5/1976 | Jacobs ................................ 604/180 |
| 4,261,303 | 4/1981 | Russo . |
| 4,392,857 | 7/1983 | Beran ................................. 604/179 |
| 4,419,097 | 12/1983 | Rowland ............................. 604/174 |

Primary Examiner—Stephen C. Pellegrino
Attorney, Agent, or Firm—Gregory W. Moravan

[57] ABSTRACT

A catheter shield comprising a dome surrounded by a peripheral, skin engaging flange. The dome defines a cavity, has a hole for the catheter, and has a radial slit extending to the edge of the shield to aid in placement of the shield around the catheter. Vents may be provided in the shield. The shield is held in place by holding the shield against the skin, moderately tensioning the catheter, providing means for preventing relative longitudinal motion between the catheter and the shield, and then releasing the catheter so the elasticity of the catheter and of the body parts which anchor it pull and hold the shield in place against the skin. A second method for securing the shield entails positioning the shield around the catheter, pressing the shield firmly downward against the skin, and applying a tape strip with one of its edges firmly against the top of the shield. When the hand pressure on the shield is released, the compressed portion of the body beneath the shield tries to expand and force the shield outwardly. However, since the tape strip prevents relative longitudinal motion between the shield and the catheter, the shield cannot move outwardly relative to the catheter and is thus held in place against the skin by the catheter and tape strip.

8 Claims, 10 Drawing Figures

CATHETER SHIELD AND METHOD OF USE

BACKGROUND OF THE INVENTION

The present invention relates to medical shields, and more particularly to a medical shield for indwelling self anchoring catheters.

SUMMARY OF THE INVENTION

Catheters, in general, are tubes or lines which are inserted through the skin into the body and include, by way of non-limiting example, arterial catheters, needle type intravenous catheters chest tubes and peritonaeal catheters. Catheters are placed in the body to obtain samples of body fluids, for drainage, for dialysis, or for the introduction of life supporting fluids and medications, for example. Indwelling catheters are those which are left in the body for extended periods of time. The catheter entrance site is where the catheter enters the body, such as through an opening made with a needle or scalpel.

Some catheters are inserted quite some distance into the body and thus become self anchoring to some extent due to the friction between the catheter and the parts of the body into which the catheter has been inserted. Frequently, a fibrous cuff is affixed to the catheter at the catheter entrance site to help ensure stability of the catheter through tissue growth to the fibrous material.

Problems with indwelling catheters are that patients frequently suffer from excoriation of the skin around the catheter entrance site due to the periodic removal and replacement of the adhesive tape often used on the skin to hold the catheter in place; and due to the periodic removal and replacement of the dressings conventionally used around the catheter entrance site, which may also tend to stick to the skin, and thus excoriate it when removed.

Patients frequently suffer from infections at the catheter entrance site due to tissue irritation caused by movement of the catheter at the catheter entrance site despite the catheter being taped in place, or due to exposure of the catheter entrance site to the environment.

In addition, excoriation of the skin around the catheter entrance site can lead to infections in the excoriated areas. Excoriation occurs due to frequent removal of the adhesive tape normally used to affix dressings to the skin and/or due to allergic reaction to components of the adhesive.

One of the objectives of the present invention is to stabilize the catheter at the catheter entrance site to help prevent its undesired movement which, in turn, helps to prevent infection at the catheter entrance site.

A further objective is to eliminate the need for adhesive tape or other adhesive media on the skin to hold the catheter in place, thereby reducing excoriation of the skin around the catheter entrance site which, in turn, reduces the chance of infection in the skin around the catheter entrance site.

Another objective is to provide a protective shield for the catheter entrance site area which can protect the site from the environment, thereby eliminating the need to use gauze pad/tape around the catheter entrance site which may adhere to the skin and cause excoriation of the skin when removed; and which can also act as a reservoir to hold medication in place around the catheter entrance site thereby also eliminating the need to use gauze pads.

It should be understood that the foregoing is a brief, not an exhaustive, summary of some of the objectives, features, advantages, and characteristics of the present invention. These and other objectives, features, advantages and characteristics of the present invention will be directly or inherently disclosed by the following, more detailed description of the present invention.

DESCRIPTION OF THE PREFERRED EMBODIMENTS

Figure 1:
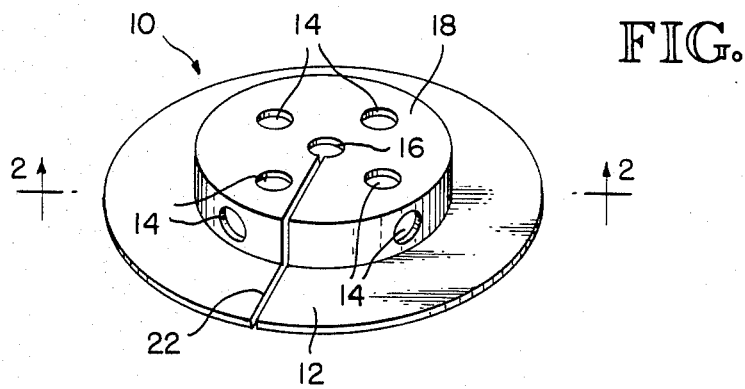
FIG. 1 is a perspective view of a first form of the present invention.
Figure 2:
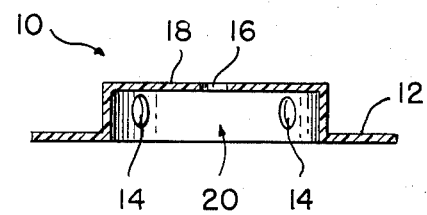
FIG. 2 is a cross sectional view thereof taken along line 2—2 of FIG. 1.

Turning now to FIGS. 1 and 2, the catheter shield 10 is vacuum formed or injection molded from, for example 0.03 inch thick polyethylene, or other suitable material which is sterilizable and which is compatible with medication, with the skin, and with other body tissues. The material chosen is relatively stiff so it can support the catheter, while still being flexible enough so it can conform to the body for patient comfort. Reinforcing ridges or other reinforcement could be used in the shield 10, as needed, to stiffen it in any desired area.

The shield 10 has a peripheral flange 12, optional air or ventilation holes 14, a catheter hole 16, a dome 18 defining a central cavity 20, and a radial slit 22. Padding, not illustrated, could be secured or used beneath the flange 12 for increased patient comfort.

Figure 7:
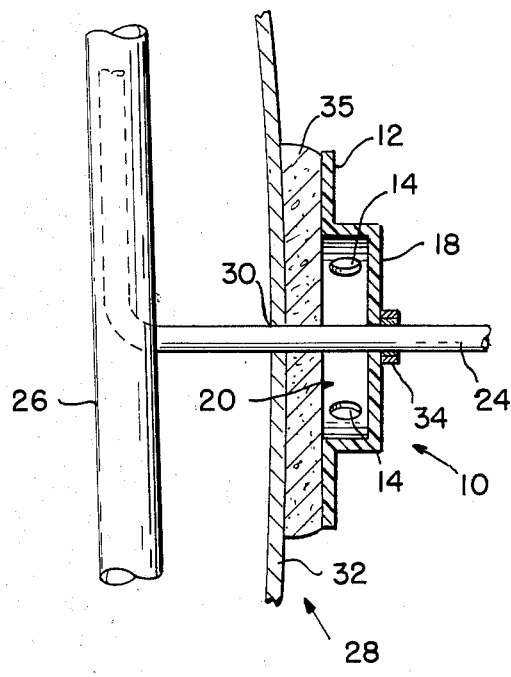
FIG. 7 is a schematic view showing the first form of the present invention in use, with portions of the view in cross section for clarity.

Referring now to FIG. 7, the shield 10 is shown in use, by way of example, with a catheter 24 which has been introduced in any conventional fashion into a vein or artery 26 in body 28 through a catheter entrance site 30 in the skin 32. After the catheter 24 is in place, the shield 10 is installed by passing the body of the catheter through the radial slit 22 in the shield until the catheter is in place in the catheter hole 16 in the shield.

To hold the shield 10 in place a moderate tension is then taken on the free end of the catheter 24 by pulling on it as though wanting to remove it, being careful not to cause the catheter to actually start to withdraw from the body. While the free end is held moderately taut, the shield is slid down the catheter against the skin and and a tape strip 34 is wrapped around the catheter adjacent the top of the shield to prevent relative longitudinal motion between the catheter and the shield. When the free end of the catheter is released, the catheter tries to withdraw into the shield due to the elasticity of the catheter and the elasticity of the body parts which anchor the catheter. However, since the tape strip prevents relative longitudinal motion between the catheter and the shield, the shield is pulled by the catheter, via the tape strip 34, snugly against the surface of the skin 32.

A second method for securing the shield entails positioning the shield 10 around the catheter 24, pressing the shield firmly downward against the skin 32, and applying a tape strip 34 with one of its edges firmly against the top of the shield. When the hand pressure on the shield is released, the compressed portion of the body beneath the shield tries to expand and force the shield outwardly. However, since the tape strip prevents relative longitudinal motion between the shield and the catheter, the shield cannot move outwardly relative to the catheter and is thus held in place against the skin by the catheter and tape strip.

Enough tape 34 is wrapped around the catheter 24 so that the catheter can not be withdrawn into the cavity 20 in the shield 10. MicroFoam brand surgical tape manufactured by the 3M Company located in Minneapolis, Minn. is suitable. It is understood, however, that any other means such as a clamp, fastener, etc., could be used in lieu of the tape to anchor the catheter and to prevent relative longitudinal motion between the catheter and the shield after the tension on the catheter is released in the first method, or after the shield is released in the second method.

After the shield 10 is in place, the radial slit 22 can be sealed, as with another piece of tape.

It is seen that the shield 10 acts to protect the catheter entrance site 30 from the entry of foreign matter, keeping it clean, dry and sanitary, eliminating the need for protective adhesively affixed gauze pads which stick to the skin and excoriate it when removed. If desired, the shield 10 may be made transparent to permit visual inspection of the entrance site. It is also seen that the cavity 20 can be filled with medication, which will be held in place around the entrance site, or that, if desired, other materials, such as a gauze pad 35 could be placed under the shield 10 or in its cavity 20.

Since the catheter hole 16 is sized to snugly receive the catheter 24, once the shield 10 is in place on the body, a major percentage of any flexing of the catheter 24 will occur at the top of the shield 10, not at the catheter entrance site. Thus, the shield stabilizes the catheter 24 at the catheter entrance site 30. This promotes healing at the entrance site and helps to prevent infection thereof.

Since the shield 10 is held in place by the catheter 24 as described earlier, it is seen that the need to use adhesive tape or other adhesive media on the skin to stabilize the catheter or gauze pads at the catheter entrance site is eliminated. This, in turn, eliminates any excoriation of the skin caused by the removal of such adhesive media, thereby helping to prevent infection in the skin around the catheter entrance site.

Use of the shield on over 100 patients has demonstrated the shield to be a sanitary means for stabilizing dressings and medication while eliminating tape-skin contact and attendant tissue damage. In all cases, badly excoriated skin around the catheter entrance site was healed in five to seven days regardless of the overall status of the patients' physical condition.

Naturally the shield 10 could be made in a variety of sizes and shapes to meet the requirements of the shield being used on any particular part of the body or with any particular catheter or other medical equipment, without departing from the scope and spirit of the present invention.

Figure 3:
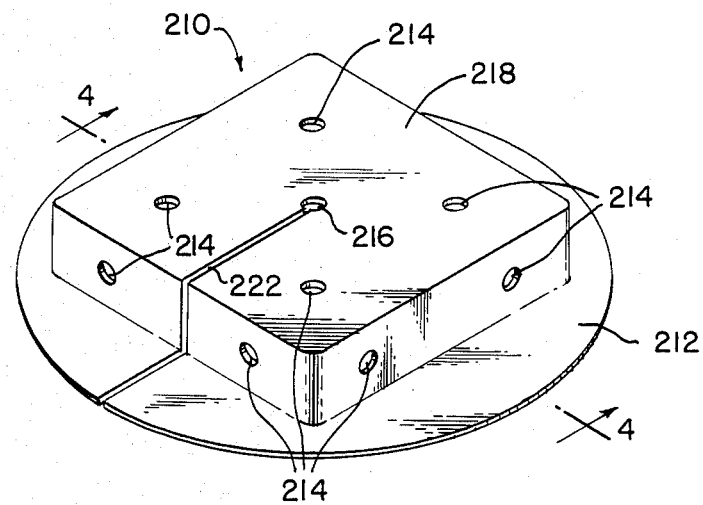
FIG. 3 is a perspective view of a second form of the present invention.
Figure 4:
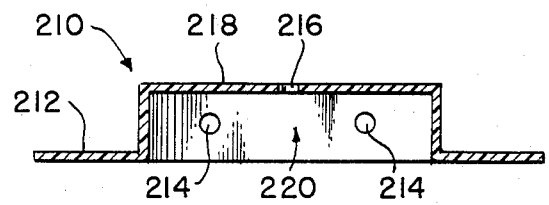
FIG. 4 is a cross sectional view thereof taken along line 4—4 of FIG. 3.

Turning now to FIGS. 3–4, a second shield 210 is shown. Since it is made and used like the shield 10, the same reference numerals have been used with a 2 prefix. The primary difference of the shield 210 is that its dome 218 is made square, and may define a cavity 220 about two inches square to more easily accommodate a common size of commercially available gauze pad. Naturally, the shield 10 or 210 could be sized to accommodate any size of gauze pad as desired.

Figure 5:
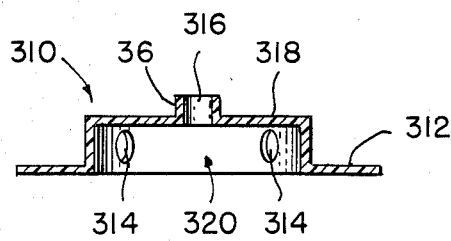
FIGS. 5 and 6 are cross sectional views of third and fourth forms of the present invention.

A third shield 310 is seen in FIG. 5 where, since it is made and used like the shield 10, the same reference numerals have been used with a 3 prefix. The primary difference of the shield 310 is that it includes an upwardly extending flange 36 extending about the catheter hole 316, to strengthen the shield 310 and to better support the catheter as it exits the shield 310.

Figure 6:
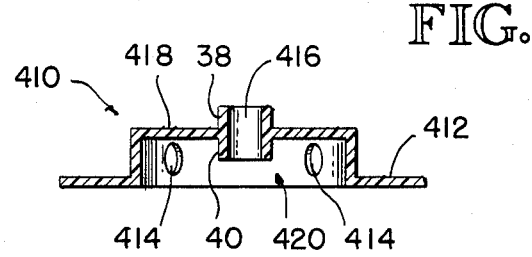

A fourth shield 410 is seen in FIG. 6 where, since it is made and used like shield 10, the same reference numerals have been used with a 4 prefix. The primary difference of the shield 410 is that it includes both upwardly and downwardly extending flanges 38, 40 about the catheter hole 416, which serve the same purpose and may be even stronger than the flange 36 of shield 310.

Figure 8:
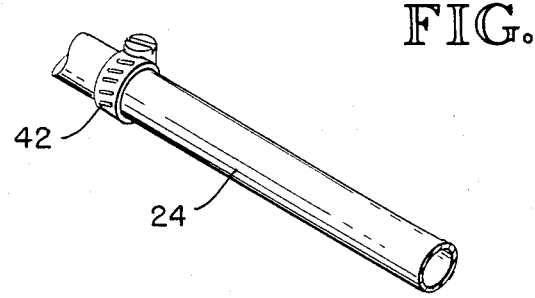
FIGS. 8–10 schematically illustrate three means for anchoring the catheter.
Figure 9:
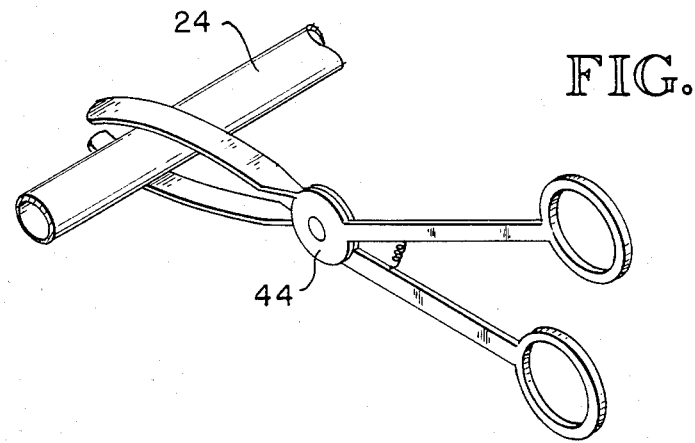
Figure 10:
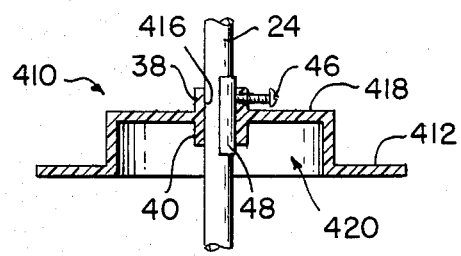

FIGS. 8–10 illustrate other means for anchoring the catheter to prevent relative longitudinal motion between the catheter 24 and the shields 10, 210, 310, 410. In FIGS. 8 and 9 the means comprise any conventional clamp or collar such as hose clamp or collar 42 (FIG. 8) or spring clamp or collar 44. Clamps or collars 42, 44 are used as was described for the tape strip 34.

In FIG. 10 the shield 410 is illustrated, by way of non limiting example, which has been suitably modified to carry a set screw 46 which selectively releases or engages the catheter 24 by means of a reinforcing plate 48 which fits over the catheter 24 and helps to prevent its collapse. Thus set screw 46 provides another means for preventing relative longitudinal motion between the catheter 24 and shields 10, 210, 310, 410.

In view of the foregoing, these and further modifications, adaptions and variations of the catheter shield of the present invention will now be apparent to those skilled in the art, within the scope of the claims which follow. It is understood the foregoing forms of the invention were shown only by way of non-limiting example.

What is claimed is:

1. A catheter shield kit, wherein said kit comprises an elastic catheter adapted to enter a body through a catheter entrance site, wherein during use a portion of said catheter is anchored in said body, and wherein during use a portion of said catheter is outside said body and is under tension;

wherein said kit further comprises a catheter anchor means and a catheter shield comprising a relatively stiff shield dome defining a shield cavity, a peripheral shield flange extending at least partially around said shield dome, and a catheter shield hole in the top of said shield dome generally aligned with said catheter entrance site;

wherein said catheter shield hole is sized to be adapted to receive said catheter therethrough;

wherein said catheter shield, during use, is adapted to be placed with said shield flange against said body, with said catheter entrance site under said shield dome, and with said catheter extending through said catheter shield hole;

wherein said catheter anchor means, during use, are for securing at least one of said catheter and said catheter shield, and wherein said catheter anchor means, during use, are adapted to prevent longitudinal motion of said catheter shield away from said body with respect to said catheter; and wherein, during use, said tension of said portion of said catheter outside said body is adapted to pull on said catheter anchor means to urge said catheter shield snugly against said body, thereby eliminating the need to use adhesive media on said body to secure said catheter shield to said body.

2. The kit according to claim 1, wherein said catheter anchor means comprises a strip of tape.

3. The kit according to claim 1, wherein said catheter anchor means comprises a collar means.

4. The kit according to claim 1, wherein said catheter anchor means comprises a clamp means.

5. The kit according to claim 1, wherein said catheter anchor means is at least partially a friction kit between said catheter and said catheter shield.

6. The kit according to claim 1, wherein said catheter anchor means includes set screw means secured to said catheter shield for selectively engaging said catheter.

7. A method of securing a shield for a catheter to a body wherein said catheter enters said body through a catheter entrance site, wherein a portion of said catheter is anchored inside said body, wherein said catheter has a free portion outside said body, and wherein the metod comprises the steps of:
providing a shield comprising a relatively stiff dome defining a cavity, a peripheral flange at least partially surrounding said dome, and a catheter hole defined by said dome;
placing at least a part of said free portion of said catheter through said catheter hole;
taking a tension on said free portion of said catheter;
locating said flange of said shield adjacent said body with said catheter entrance site beneath said dome;
providing means for preventing longitudinal motion of said catheter shield away from said body with respect to said catheter; and
releasing at least some of said tension on said free portion of said catheter;
wherein after said tension on said free portion of said catheter is at least partially released, said catheter pulls said shield against said body and holds said shield snugly in place on said body.

8. A method of securing a shield for a catheter to a body wherein said catheter enters said body through a catheter entrance site, wherein a portion of said catheter is anchored inside said body, wherein said catheter has a free portion outside said body, and wherein the method comprises the steps of:
providing a shield comprising a relatively stiff dome defining a cavity, a peripheral flange at least partially surrounding said dome, and a catheter hole defined by said dome;
placing at least a part of said free portion of said catheter through said catheter hole;
locating said flange of said shield adjacent said body with said catheter entrance site beneath said dome;
compressing the portion of said body beneath said shield by pressing said shield firmly against said body;
providing means for preventing longitudinal motion of said catheter shield away from said body with respect to said catheter when ceasing to press said shield firmly against said body; and
ceasing said compressing of said portion of said body beneath said shield by ceasing to press said shield firmly against said body;
wherein after ceasing to press said shield firmly against said body, said catheter helps to prevent outward movement of said shield away from said body to hold said shield snugly in place on said body.

* * * * *

UNITED STATES PATENT AND TRADEMARK OFFICE
CERTIFICATE OF CORRECTION

PATENT NO. : 4,516,968

DATED : May 14, 1985

INVENTOR(S) : Charles A. Marshall et al.

It is certified that error appears in the above-identified patent and that said Letters Patent is hereby corrected as shown below:

Claim 5, line 2, "kit" should read -- fit --.

Claim 7, line 5, "metod" should read -- method --.

Signed and Sealed this

Twenty-ninth Day of September, 1987

Attest:

DONALD J. QUIGG

Attesting Officer

Commissioner of Patents and Trademarks